United States Patent [19]

Chi et al.

[11] 4,450,291

[45] May 22, 1984

[54] DECONTAMINATION OF KA OIL REFINEMENT WASTE STREAM

[75] Inventors: Ching T. Chi; J. Harvey Lester, Jr., both of Pensacola, Fla.

[73] Assignee: Monsanto Company, St. Louis, Mo.

[21] Appl. No.: 490,636

[22] Filed: May 2, 1983

[51] Int. Cl.³ ............................................. C07C 51/245
[52] U.S. Cl. .................................... 562/530; 562/527; 562/528; 562/529
[58] Field of Search ............... 562/527, 528, 529, 530; 260/705

[56] References Cited

U.S. PATENT DOCUMENTS

| | | | |
|---|---|---|---|
| 2,703,331 | 3/1955 | Goldbeck, Jr. et al. | 562/529 |
| 2,931,834 | 4/1960 | Crouch | 260/586 |
| 2,938,924 | 5/1960 | Simon et al. | 260/586 |
| 3,023,238 | 2/1962 | Chapman et al. | 260/533 |
| 3,109,860 | 11/1963 | Lidov et al. | 260/586 |
| 3,260,742 | 7/1966 | Hogeman | 260/533 |
| 3,423,471 | 1/1969 | Golden et al. | 260/617 |
| 3,492,355 | 1/1970 | Olenberg et al. | 260/586 |
| 3,551,482 | 12/1970 | Gey et al. | 562/529 |
| 3,576,856 | 4/1971 | Davis | 562/530 |
| 3,810,937 | 5/1974 | Kuceski | 562/530 |

Primary Examiner—Natalie Trousof
Assistant Examiner—Bruce D. Gray
Attorney, Agent, or Firm—Thomas Y. Awalt, Jr.

[57] ABSTRACT

A process for the decontamination of the distillation refinement residue from the process of oxidizing cyclohexane to KA oil is provided. The process comprises washing the distillation refinement residue with the crystallization by-product obtained in crystallizing adipic acid from the product stream of the process of oxidizing the KA oil with a strong acid. This crystallization residue comprises residual amounts of the strong acid and adipic acid, as well as substantial amounts of glutaric acid and succinic acid.

14 Claims, 1 Drawing Figure

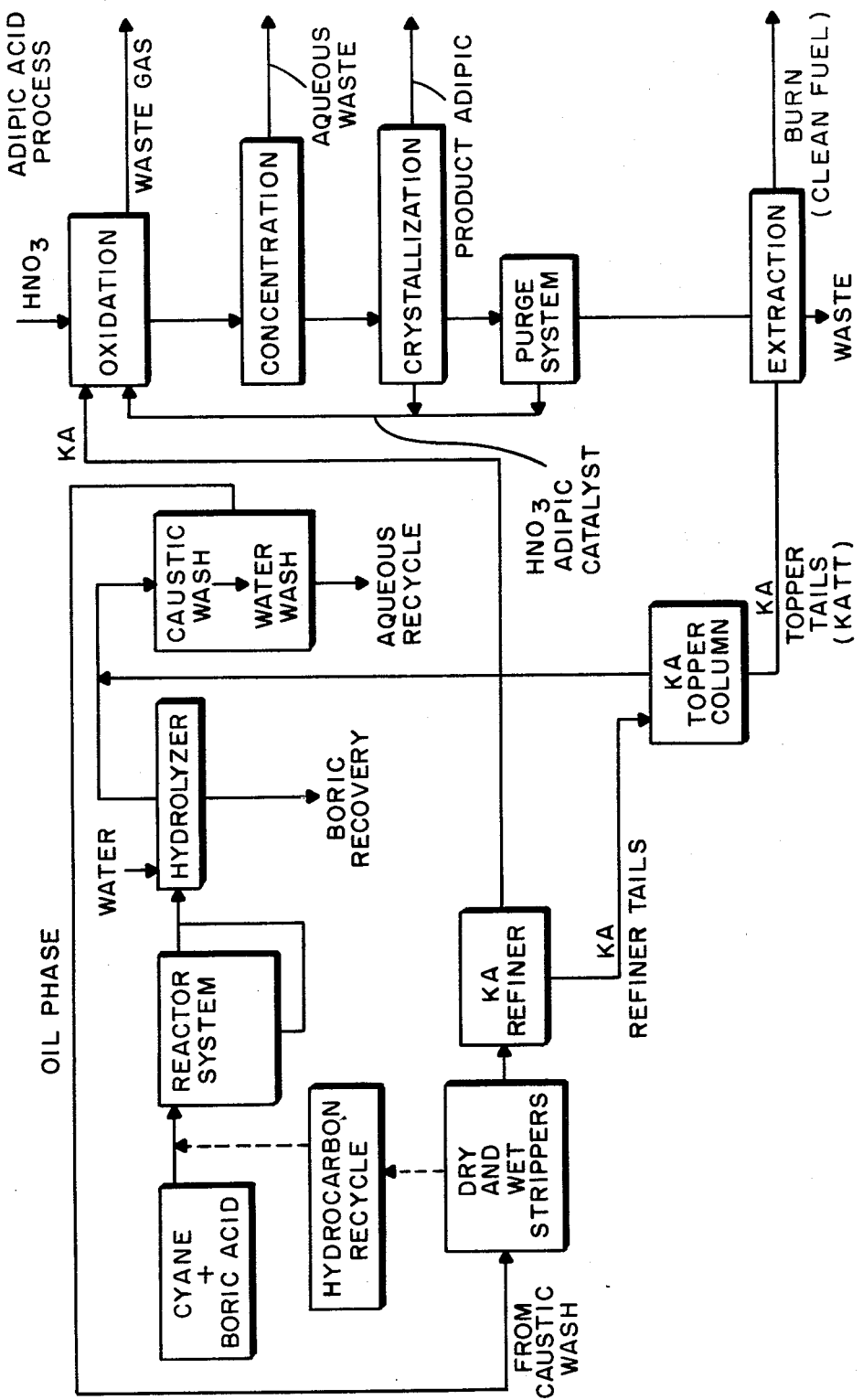

DECONTAMINATION OF KA OIL REFINEMENT WASTE STREAM

BACKGROUND OF THE INVENTION

A. Field of the Invention

The invention relates to the manufacture of KA oil (cyclohexanol and cyclohexanone), and particularly to a by-product of the manufacture of KA oil which is the distillation refinement residue. According to this invention, the distillation refinement residue is washed with a by-product stream, which is the crystallization residue from the crystallization of adipic acid from the product stream of a process for producing adipic acid from KA oil by oxidizing the KA oil with a strong oxidizing acid.

B. The Prior Art

A well known and commercial method of producing adipic acid, a valuable and widely used chemical, involves a series of steps including (1) the oxidation of cyclohexane in a liquid phase with air or other molecular oxygen-containing gas to a mixture of cyclohexanol and cyclohexanone at rather low conversion but high yields, (2) the separation of the unoxidized cyclohexane from the cyclohexanol and cyclohexanone intermediate reaction product, (3) the final oxidation of the intermediate material with a strong oxidizing agent such as nitric acid into adipic acid and minor amounts of other organic dibasic acids such as glutaric acid and succinic acid, and (4) isolation of the adipic acid from the by-product organic acids. A preferred method of carrying out the cyclohexane oxidation is in the presence of a boron compound such as boric acid. A preferred method of carrying out the nitric acid oxidation of the said intermediate reaction product involves the use of a mixed catalyst system composed of vanadium and copper compounds. The adipic acid so produced is crystallized from the nitric acid oxidation product and separated from the adipic acid mother liquor. Contained in the mother liquor are the valuable catalyst compounds and soluble by-product organic dibasic acids.

Purification of the cyclohexanol and cyclohexanone intermediate reaction product has involved from time to time and may include all, or any combination of, the following process steps:

(1) deperoxidizing cyclohexyl hydroperoxide contained in the crude product stream;
(2) hydrolyzing the crude product stream with water, thereby to de-esterify boric esters, and thereafter decant to remove boric values;
(3) extracting the product stream with caustic thereby to provide an oil phase containing the product and leaving an aqueous phase comprising impurities;
(4) stripping the product stream to remove and recycle cyclohexane.

After all or any combination of the above steps have been accomplished, one or more of the following have been common practice in the prior art:

(5) refining the product stream to remove the product KA leaving behind a refinement residue, and
(6) refining the refinement residue so as to remove additional product KA leaving behind a second refinement residue. When water or steam has been employed in the above process steps, this second refinement residue contains an organic phase and an aqueous phase of variable quantities. The organic phase consists primarily of high boiling point components which have been purged as waste material. It has a gross heating value in the range of from approximately 12,500 to 13,500 btu/lb (29154.6 to 31369.6 joules/gram). In its form as a waste product stream, it is difficult to use as fuel because it is in two phases of variable proportions and because it contains materials, such as sodium, boron and compounds thereof, which cause atmospheric contamination and serious refractory corrosion and boiler tube fouling.

Any method by which the KA waste stream could be employed as a safe and effective fuel would be a significant advance in the art and is an object of this invention.

SUMMARY OF THE INVENTION

According to this invention the waste stream from adipic acid manufacturing is used to decontaminate the above described second refinement residue.

According to this invention, the refinement residue is the residue from the process comprising air oxidizing cyclohexane to KA oil in the presence of a boron compound such as boric acid to provide a crude product stream comprising cyclohexanol, cyclohexanone, cyclohexane and boric esters; and where the crude product stream is subjected to:

(1) a hydrolyzing step in which water is added to the stream to de-esterify boric esters followed by a decantation thereby to remove boric values;
(2) a caustic wash step in which the stream is extracted with caustic thereby to provide an oil phase containing the product and leaving an aqueous phase comprising impurities;
(3) a stripping step in which the stream is stripped to remove cyclohexane for recycle;
(4) one or more refining steps in which the stream is refined to remove the product KA leaving behind a refinement residue.

In a preferred version of the process for the production of KA oil, the crude product stream is subjected to a deperoxidizing step before the hydrolyzing step in which the cyclohexyl hydroperoxide is deperoxidized.

Also in a preferred version there are two refining steps rather than one, and the refinement residue is the refinement residue of the second refining step, which is a steam distillation. The refinement residue comprises high boiling organics, boron and caustic.

We have discovered that this refinement residue can be decontaminated, primarily through removal of boron and sodium, as well as the aqueous phase referred to above, by washing with a dibasic acid by-product stream from the process in which the product KA oil is oxidized with a strong oxidizing acid into a product stream comprising adipic acid with minor amounts of glutaric and succinic acids. Surprisingly, during the course of the wash, a consistent specific gravity differential of about 0.02 between the aqueous and organic phases of the refinement residue is maintained. This differential may help explain how the aqueous phase is effectively removed. The dibasic acid waste stream residue comprises glutaric acid, succinic acid, residual amounts of any catalyst such as vanadium and/or copper and residual amounts of adipic acid and the strong oxidizing acid, preferably nitric acid, and water. The mineral acidity of this waste stream may enhance sodium extraction by a liquid-liquid ion exchange. Typical concentrations of organic acids in such streams are 2–5 eq/liter.

The dibasic acid waste stream is the principal waste stream involved in the production of adipic acid, involving the following steps which are well known in the art:

(1) removal of most of the strong oxidizing acid (preferably nitric acid) and
(2) a crystallization step in which the adipic acid is crystallized out of the product stream leaving the by-product stream.

In a preferred version of this process, the removal of most of the strong oxidizing acid follows a first crystallizing step in which adipic acid is crystallized leaving a mother liquor rich in the strong oxidizing acid which is removed in an evaporation step before the second crystallization in which the adipic acid is removed, leaving behind a stream from which any further catalyst is recovered by ion exchange (copper and vanadium being a preferred catalyst in this reaction), leaving behind the dibasic acid by-product stream which in turn is used for washing and decontaminating the refinement residue.

In the detailed description, reference will be made to the drawing in which the FIGURE is a flow sheet of the process.

DETAILED DESCRIPTION OF THE INVENTION

Referring now in greater detail to the process for producing the intermediate KA oil from which the stream to be decontaminated is produced, a preferred version of this process is shown schematically at the FIGURE.

Cyclohexane (cyane) and boric acid are introduced into a series of reactors in which, with related equipment and in accordance with techniques well known in the art, a product stream is produced containing cyclohexanol, cyclohexanone, cyclohexane and boric esters. The esters are de-esterified in a hydrolyzer permitting recovery of boric values through decantation and crystallization. The remainder of the stream may then be caustic washed in accordance with techniques well known in the art to provide an oil phase containing the adipic precursor and an aqueous phase containing impurities. The aqueous phase is then removed by decantation. The oil phase from the caustic wash then goes to a series of strippers in which cyclohexane is removed and recycled to the reactor system. The remainder of the oil phase is fed to a KA refiner from which KA is taken for nitric acid oxidation, and from which the refiner tails are conducted to a KA topper column. A second refinement takes place in the KA topper column from which recovered KA is conducted to the caustic wash step leaving the KA topper tails as the principal ultimate residue.

The KA topper tails are washed with the dibasic acid by-product stream from the process of oxidizing KA oil with a strong acid (nitric). As shown in the flow sheet (of the Drawing), after the nitric acid oxidation and the removal of dissolved gases, which are predominantly nitrogen oxide gases, the product stream is concentrated, thereafter crystallized, leaving behind a mother liquor rich in nitric acid, the major portion of which is removed by evaporation before a second crystallization is used to separate the remaining product adipic acid from the dibasic acid by-product stream, which in turn is used for washing and decontaminating the refinement residue. On the flow sheet (Drawing), the term "purge system" is used to generically describe the evaporation of the nitric acid and the second crystallization of adipic acid and recovery of metal catalysts from the mother liquor.

Any method for the preparation of adipic acid from KA oil in which a strong oxidizing acid is employed to oxidize the KA oil into adipic and where most of the strong acid is subsequently removed from the product stream; and where the product stream is subsequently crystallized thereby to remove the adipic acid leaving a by-product stream comprising glutaric acid, succinic acid, residual amounts of adipic acid, the strong oxidizing acid and water, is satisfactory. Preferred are any of such processes employing as a strong acid, nitric acid. It is desirable that there be a density differential between the by-product stream and the residue.

We have discovered that where the refinement residue of the process for making the KA oil is washed with the dibasic acid by-product stream from the process for making adipic acid from KA oil, the refinement residue is decontaminated and thereby rendered reasonably non-corrosive and safe for use as a fuel.

Any method of washing can be used which provides for intimate contact between the liquid materials in each of the streams. The volume of the wash liquid is desirably adjusted so as to provide a volume ratio of the wash liquid to the refinement residue of about 0.5–10.0 with a preferred and typical ratio of 0.5–2.0. A higher volume ratio will wash well but will result in a waste of the by-product stream. It is preferable, although not necessary, to heat the refinement residue before exposure to the wash stream. The preferred temperature of the refinement residue is 30°–40° C. The temperatures of both streams are selected to maximize the density difference and to minimize the reactions between the organics and the nitric acid contained in the wash stream and to prevent solid formation in the wash stream. A preferred temperature of the wash stream is 25°–30° C. Any commercial centrifugal extractor may be used for the wash step. A centrifugal extractor is preferred because it shortens the contact time and so minimizes reactions during the wash step. A mixer/settler combination or packed extraction column can be used in lieu of the centrifugal extractor for efficient washing.

Wherever in this specification removal of "most of the strong acid from the product stream" is specified, by "most" is meant: 70–99.99%.

We claim:

1. A process for the decontamination of a waste stream refinement residue from the process comprising oxidizing cyclohexane to KA oil, the waste stream residue comprising high boiling organics, and caustic, the process comprising washing the residue with a by-product of the process comprising:
    (a) oxidizing KA oil with a strong oxidizing acid into a product stream comprising adipic acid with minor amounts of glutaric and succinic acids and the strong acid;
    (b) removal of most of the strong acid from the product stream;
    (c) crystallizing adipic acid from the product leaving the by-product stream comprising glutaric acid, succinic acid, residual amounts of adipic acid, residual amounts of the strong oxidizing acid, and water.

2. The process of claim 1 wherein the oxidation of cyclohexane is in the pressure of boric acid and both waste stream residue and by-product streams further include residual amounts of the boric acid.

3. The process of claim 1 wherein the strong oxidizing acid is nitric acid and the by-product stream further includes nitric acid.

4. The process of claim 3 wherein the by-product stream further includes residual amounts of copper and vanadium.

5. The process of claim 1 wherein the oxidation of the cyclohexane is in the presence of boric acid, the strong oxidizing acid is nitric acid and the by-product stream contains residual amounts of both boric acid and nitric acid.

6. The process of claim 1 wherein the organic acid concentration in the by-product stream is 2-5 eq/liter.

7. The process of claim 1 wherein the volume ratio of the by-product stream to the refinement residue is 0.5-10.0.

8. The process of claim 1 wherein the volume ratio of the by-product stream to the refinement residue is 0.5-2.0.

9. A process for the conversion of the refinement residue from the process comprising:
   (a) air oxidizing cyclohexane to KA oil in the presence of boric acid to provide a crude product stream comprising cyclohexanol, cyclohexanone, cyclohexane and boric esters;
   (b) hydrolyzing the stream with water to de-esterify boric esters and thereafter decant to remove boric values;
   (c) extracting the stream with caustic to provide an oil phase containing the product and leaving an aqueous phase comprising impurities;
   (d) stripping the oil phase to remove cyclohexane for recycle;
   (e) one or more refining steps of the stripped oil phase whereby the product KA is removed leaving a refinement residue,
the process comprising washing the refinement residue with a by-product of the process comprising:
   (a) oxidizing the product KA oil with a strong oxidizing acid into a product stream comprising glutaric acid, succinic acid, adipic acid and the strong oxidizing acid;
   (b) removing most of the strong oxidizing acid;
   (c) crystallizing adipic acid from the product stream leaving the by-product stream comprising glutaric acid, succinic acid, residual amounts of adipic acid and residual amounts of the strong oxidizing acid.

10. The process of claim 9 wherein the strong oxidizing acid is nitric acid and the by-product stream further includes nitric acid.

11. The method of claim 9 wherein the oxidizing of cyclohexane to KA oil is in the presence of copper and vanadium and wherein the by-product stream further includes residual amounts of copper and vanadium.

12. The method improvement of claim 9 wherein the organic acid concentration in the by-product stream is 2-5 eq/liter.

13. The process of claim 9 wherein the volume ratio of the by-product stream to the refinement stream is 0.5-10.

14. The process of claim 9 wherein the volume ratio of the by-product stream to the refinement stream is 0.5-2.0.

* * * * *